United States Patent [19]

von Recum et al.

[11] Patent Number: 4,846,834
[45] Date of Patent: Jul. 11, 1989

[54] METHOD FOR PROMOTING TISSUE ADHESION TO SOFT TISSUE IMPLANTS

[75] Inventors: Andreas F. von Recum; Francis W. Cooke, both of Clemson, S.C.

[73] Assignee: Clemson University, Clemson, S.C.

[21] Appl. No.: 168,894

[22] Filed: Mar. 16, 1988

Related U.S. Application Data

[62] Division of Ser. No. 868,118, May 27, 1986, abandoned.

[51] Int. Cl.[4] .............................................. A61F 2/02
[52] U.S. Cl. ........................................ 623/11; 623/66; 427/2
[58] Field of Search ................... 623/11, 12, 16, 66, 623/1, 2, 13–15; 427/2, 37, 40, 50, 13; 430/128, 131; 128/335.5

[56] References Cited

U.S. PATENT DOCUMENTS

| | | | |
|---|---|---|---|
| 3,557,795 | 1/1971 | Hirsch | 128/335.5 |
| 3,677,795 | 7/1972 | Bokros et al. | 117/46 |
| 3,952,334 | 4/1976 | Bokros et al. | 623/66 |
| 4,149,277 | 4/1979 | Bokros | 623/66 |
| 4,272,855 | 6/1981 | Frey | 623/16 |
| 4,374,669 | 2/1983 | MacGregor | 427/2 X |
| 4,531,916 | 7/1985 | Scantlebury et al. | 433/173 |
| 4,588,667 | 5/1986 | Jones et al. | 430/128 X |

FOREIGN PATENT DOCUMENTS

86/02804  5/1986  PCT Int'l Appl. .

*Primary Examiner*—Alan W. Cannon
*Attorney, Agent, or Firm*—Dority & Manning

[57] ABSTRACT

A soft tissue implant comprises a flexible main body portion, having tissue-facing surfaces and a thin layer of pure titanium covering the tissue-facing surfaces. A method of promoting tissue adhesion of a soft tissue host to the tissue-facing surfaces of a soft tissue implant comprising a strip of polyethylene terephthalate velour comprises the steps of cleaning the strip with a low-residue detergent and rinsing same with fresh distilled water; refluxing the strip in distilled water for one hour at a temperature of less than 30° C.; drying the strip in a room-temperature desicator for several days; sterilizing the strip and packaging same; degasing the strip and storing same in a dust-free environment; removing the strip from the packaging and mounting the strip in a vacuum evaporator at an approximate angle of incidence of 90° from a pure titanium metal evaporant; evacuating the vacuum evaporator to a vacuum of about $2 \times 10^{-5}$ Torr; evaporating the titanium by direct resistence heating same; coating the strip with a layer of pure titanium on the order of one micron thick; and resterilizing and implanting the titanium-coated strip into the tissue host.

12 Claims, 5 Drawing Sheets

METHOD FOR PROMOTING TISSUE ADHESION TO SOFT TISSUE IMPLANTS

This is a division of application Ser. No. 06/868,118 filed May 27, 1986, now abandoned.

BACKGROUND OF THE INVENTION

1. Field of the Invention

The present invention relates to soft tissue implants, and in particular to a method for promoting tissue adhesion to soft tissue implants.

2. Prior Art

Most foreign bodies entering or contacting living tissue cause the tissue in contact therewith to form an interface with the foreign body comprising inflammatory tissue normally associated with wound healing. Some materials are biocompatible in that they cause minimal and transient formation of inflammatory tissue when implanted into living tissue. Examples of biocompatible materials are: aluminum, carbon, and titanium. Thus, all three are common materials used for hard tissue implants. Since titanium is rather expensive, it is sometimes applied as a coating to another, less expensive rigid material in forming a hard tissue implant.

Polymeric materials can be sufficiently elastic for use as soft tissue implants. However, polymeric materials are generally not sufficiently biocompatible to be used as the portion of an implant that contacts the tissue. Accordingly, carbon or aluminum has been applied to the surface of a polymeric substrate to improve the histocompatibility and vascular graft patency of the resulting implant. The best results have been obtained using a carbon surface coating, which has been applied to polymeric surfaces comprising both hard tissue implants, such as in U.S. Pat. No. 3,952,334 to Bokros et al, and to a soft tissue suture, such as in U.S. Pat. No. 4,149,277 to Bokros. Aluminum also has been vaporized and vapor deposited on a suture made of Dacron in U.S. Pat. No. 3,557,795 to Hirsch. However, being a stiff metal, titanium is not suitable for the design of pliable, soft implant devices which would be required for the development of vascular grafts, percutaneous implants or other materials desired in plastic and reconstructive surgery.

As a coating material, carbon is preferred to aluminum, because aluminium tends to dissolve as it reacts with the surrounding tissue. However, aluminum adheres better to a polymeric substrate, while carbon tends to chip off easily. Since titanium tends to bond chemically with a polymeric substrate, a small proportion o titanium has been mixed with pyrolytic carbon to form a coating on a substrate material such as artificial graphite, boron carbide, silicon carbide, tantalum, molybdenum, tungsten and various ceramics such as mullite. This mixture of carbon and titanium to form a substrate coating for a hard tissue implant is disclosed in U.S. Pat. No. 3,677,795 to Bokros et al.

Titanium is generally recognized as one of the most tissue compatible materials presently available. Titanium has been reported to be a highly histocompatible hard tissue implant material in many applications. Titanium appears to have a stimulatory effect on connective tissue cell proliferation, and cellular adhesion to titanium has been postulated by others. Kasemo, "Biocompatibility of Titanium Implants: Surface Science Aspects," *J. Prosth. Dent.*, 48: 487–494 (1982) and Albrektsson et al, "The Interface Zone of Inorganic Implant in vivo: Titanium Implant in Bone," *Ann. Biomed. Engr.* 11:1–27 (1983).

The effect on soft tissue ingrowth of altering the surface of an implant has been studied. Perhaps the best known surface alteration is achieved by coating polyethylene terephthalate (PET) with a carbon layer. For example, vacuum evaporating carbon on a velour fabric results in an implant that can be employed as vascular grafts, prosthetic fabrics and prosthetic heart valve sewing rings. Although carbon-coated PET velour fabric vascular grafts showed relatively higher patency rates than the non-coated prostheses, the carbon-coated fibers appeared to show no histological difference in the elicited tissue response when compared to non-coated PET velour fabric fibers. Aluminum also has been evaporated onto the surface of PET velour fabric vascular prostheses, and a similarly slight increase in patency rate was observed.

Implants with surface irregularities have been shown to promote aggressive macrophage activity. The effects of textured surfaces on interfacial cells, namely mononuclear phagocytes, include a change of infiltration of these cells, an increase in adhesion, vacuolization, filopodia formation, cytoplasmic-to-nuclear ratio, metabolism and enzyme activity. Foreign body giant cell formation augmented further the intensity of this response and indicated poor tolerance of the host tissue to the implant. Comparison of the tissue responses of abraded surfaces to smooth surfaces reveals a similar local increase in the population of macrophages around the abraded implants. In addition to being proliferative, these cells secreted high concentrations of enzymes such as leucine aminopeptidase, which suggested rapid tissue turnover.

Surfaces which were effective in the promotion of tenacious bio-adhesion required critical surface tensions between 30 and 40 dynes/cm. Fibroblast adhesion, spreading and growth were directly related to surface free energy of hydrophilic materials such as titanium, gold, nickel, hydroxylapatite, and glass.

In some cases, the contact angles of hydrophobic materials which are immersed in protein-containing serum appear to converge relatively close to that obtained for hydrophilic materials. A few well known biomaterials, carbon, poly-methylmethacrylate (PMMA), poly-tetra-fluoro-ethylene (PTFE) and PET, possess such ability. However, in a recent study of the response of rat tail fibroblasts, it was found that the change in surface energy of these substrates had no significant effect on cell morphology or growth rate. Instead, the study identified fiber diameter and surface topography of these materials as the two factors which influenced the morphologies of the fibroblasts.

A porous PET velour textile has been used as a replacement for blood vessels, and other textile biomaterials have been employed in various applications of soft tissue prostheses. There are a number of anatomical sites where PET velour fabric is now commonly used as a soft tissue replacement material. The local tissue response to PET velour fabric has been investigated at percutaneous, subcutaneous, and vascular implantation sites. In general, the tissue bed forms a connective tissue capsule around the implant. During the healing process, tissue extends into the implant's interstices and thus causes a direct attachment of the implant to the capsule, anchoring the implant to the host tissue. Normally, this anchoring is not observed with solid implants.

However, combined light and electron microscopic studies of the soft tissue in growth for PET velour fabric have demonstrated a high degree of cellularity, a scarcity of fibroblasts, and the presence of a delicate connective tissue matrix in the implant interstices, even after prolonged implantation periods in the subcutaneous tissue. This ingrown granulation tissue was found to be neither adherent to nor supportive of the individual PET velour fabric fibers and did not fulfill the initial design purpose of implant anchorage.

OBJECTS AND SUMMARY OF THE INVENTION

The principal object of the present invention is to provide a method for promoting tissue adhesion to soft tissue implants without impairing the biocompatibility of the implants.

Another object of the present invention is to provide a method for promoting connective tissue adhesion to a soft tissue implant for purposes of anchoring the implant to the host's tissue bed.

Additional objects and advantages of the invention will be set forth in part in the description which follows, and in part will be obvious from the description or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, the method of promoting tissue adhesion of a host's soft tissue bed to a soft tissue implant having a main body portion with tissue-facing surfaces, comprises the steps of: coating the tissue-facing surfaces of the main body portion with a layer of pure titanium; sterilizing the coated implant; and implanting the implant in the host's soft tissue bed. Preferably, the coating step comprises vapor deposition of titanium on the tissue-facing surfaces of the main body portion. The main body portion preferably is comprised of a polymeric material, at least on the tissue-facing surfaces thereof.

In an alternative embodiment of the present invention, the tissue-facing surfaces are formed of a porous polymeric material in which the pores have diameters in the range of 1 to 150 microns.

In another alternative embodiment of the present invention, the tissue-facing surfaces of the polymeric material comprise a roughened surface texture of hills and valleys of depths and widths in a range of one-hundredth to one-tenth of one micron.

In a further alternative embodiment of the present invention, the soft tissue implant has tissue-facing surfaces formed of polymeric fibers, including woven, knitted, felted, spun-bonded, heat-bonded, velvet or velour fabrics.

In yet another alternative embodiment of the present invention, the soft tissue implant comprises a pliable strip of material which is capable of adhering to a thin layer of pure titanium.

The accompanying drawings, which are incorporated in, and constitute a part of this specification, illustrate exemplary embodiments of the invention, and together with the description, serve to explain the principles of the invention.

BRIEF DESCRIPTION OF THE DRAWINGS

FIG. 12 is an expanded cross-sectional view taken along the lines 12—12 of FIG. 11a;

DESCRIPTION OF THE PREFERRED EMBODIMENTS

Reference will now be made in detail to the present preferred embodiments of the invention, examples of which are illustrated in the accompanying drawings.

Figure 1:
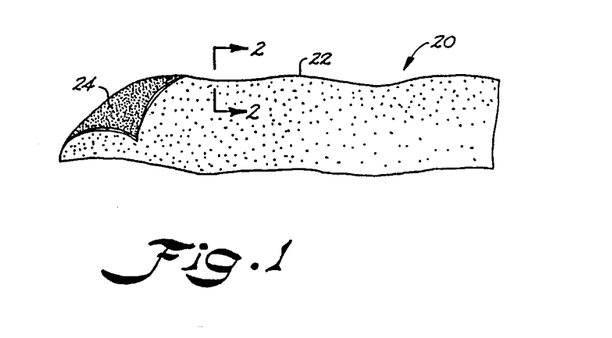
FIG. 1 is a top plan view of an embodiment of the apparatus of the present invention with the upper left hand corner turned over.
Figure 2:
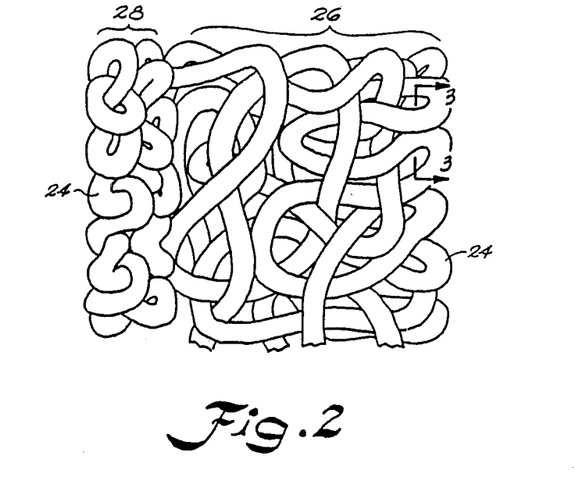
FIG. 2 is an expanded cross-sectional view taken along the lines 2—2 of FIG. 1.

In accordance with the apparatus of the present invention, a soft tissue implant comprises a flexible main body portion having tissue-facing surfaces. As embodied herein and shown for example in FIG. 1, a main body portion is designated generally by the numeral 20. Main body portion 20 can comprise a fabric 22 formed of polyethylene terephthalate (PET) fibers 24 which have been woven, spun bonded, felted, or knitted. The fabric can be woven, felted, spun bonded, knitted or otherwise processed into varying configurations, porosities and wall thicknesses. As shown in FIG. 2, the fabric constitutes a warp knit velour which has a velour surface portion 26 appearing as loops and whorls of fibers 24 and a tight-knit backing 28 consisting of compactly arranged PET fibers 24.

In one embodiment of the velour used in the EXAMPLE described below, the thickness of the velour fabric is 1 mm and the mean distance between PET fibers on the velour surface side is 48 microns, plus or minus 34 microns. The mean distance between PET fibers on the backing side is 15 microns, plus or minus 10 microns. The porosity of the velour fabric is 2,000 $cm^3$ of water per $cm^2$ per minute at a pressure of 120 Torr.

Figure 3:
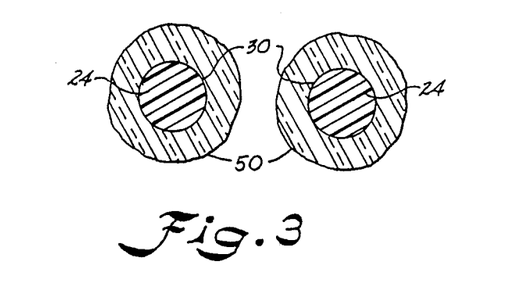
FIG. 3 is an expanded cross-sectional view taken along the lines 3—3 of FIG. 2.

The tissue-facing surfaces of the main body portion constitute the exterior surfaces of the main body portion. The tissue-facing surfaces are those surfaces of the main body portion that would be exposed to contact with the tissue of the host tissue in the absence of any intervening coating or covering layer that separates the tissue-facing surfaces from the host tissue. For example, in the velour fabric shown in FIG. 3, the tissue-facing surfaces include the cylindrical exterior surfaces of each looped fiber 24 of PET and are designated by the numeral 30.

In another preferred embodiment of the present invention, the main body portion can comprise a substrate formed of a flexible polymeric material. The main body portion must be formed of a material having sufficient elastic properties to undergo whatever structural deformation is required at the site of the implantation. The configuration of the main body portion can be a rod, a strip, a disk, or a plate. Moreover, each of the foregoing can be straight, curved, flat planar, or a curved surface. Preferably, the main body portion is formed of a polymeric material such as PET, PMMA and PTFE.

In further accordance with the soft tissue implant of the present invention, the tissue-facing surfaces of the main body portion are covered by a thin film or layer 50 of about 1 micron thickness of pure titanium. See FIGS. 3, 6, 8, 10, 12, 14 and 16.

Applicants recognize that the term "pure" as applied to titanium requires some explanation. Chemical purity means as pure as possible without the application of heroic means to eliminate or prevent impurities. The titanium purity required for practicing the present invention need not be as pure as chemical purity. Commercial purity is the next highest level of purity to chemical purity and translates into a purity of titanium having traces of oxygen for example, on the order of 1,000 parts per million. The purity of titanium for practicing the present invention is also less than the purity required for commercial purity. As long as there is no intentional introduction of contaminants to the titanium used to practice the present invention, the titanium is likely to be sufficiently pure for purposes of practicing the present invention.

Figure 5:
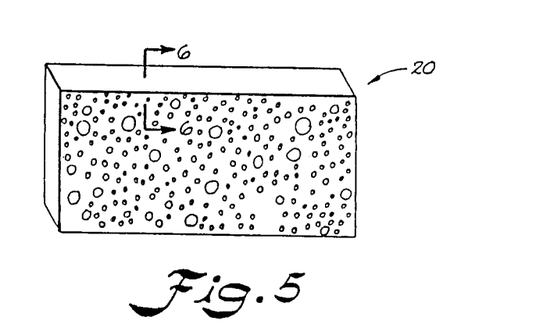
FIG. 5 is a perspective view of another embodiment of the apparatus of the present invention.
Figure 6:
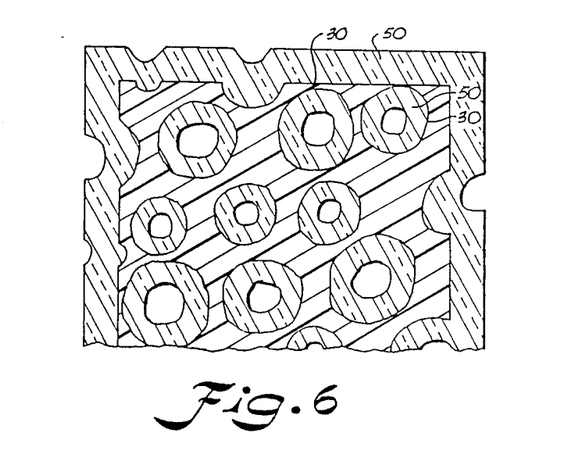
FIG. 6 is an expanded cross-sectional view taken on the lines 6—6 of FIG. 5.

As shown in FIGS. 5 and 6, in yet another embodiment of main body portion 20 of the present invention, the tissue-facing surfaces can be formed of a porous polymeric material. In such embodiments, tissue-facing surfaces 30 are configured like the surfaces of a sponge. A thin layer 50 of pure titanium coats tissue-facing surfaces 30.

Figure 7:
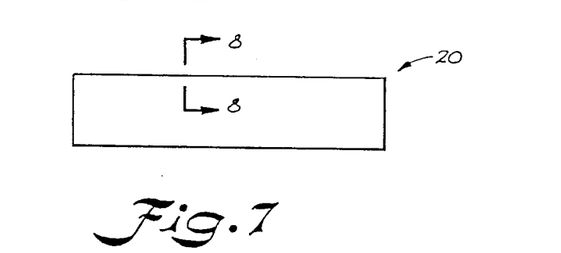
FIG. 7 is a perspective view of another alternative embodiment of the apparatus of the present invention.
Figure 8:
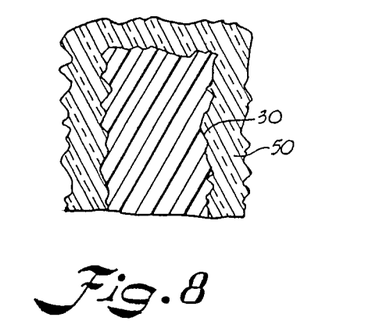
FIG. 8 is an expanded cross-sectional view taken along the lines 8—8 of FIG. 7.

As shown in FIGS. 7 and 8, in another alternative embodiment of main body portion 20 of the present invention, tissue-facing surfaces 30 are formed of a polymeric material having a roughened surface texture. The roughness of the surface texture is characterized by hills within a height range of 1 to 150 microns. The surface texture also is characterized by valleys having depths within a range of 1 to 150 microns. The widths of the hills and valleys also fall within a range of 1 to 150 microns. Tissue-facing surfaces 30 are coated by a thin layer 50 of pure titanium.

Figure 9:
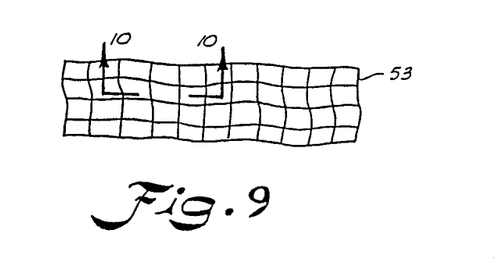
FIG. 9 is a top plan view of yet another alternative embodiment of the apparatus of the present invention.
Figure 10:
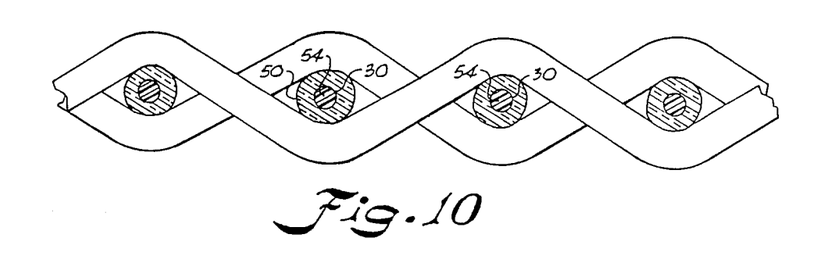
FIG. 10 is an expanded cross-sectional view taken along the lines 10—10 of FIG. 9.

As shown in FIGS. 9 and 10, in another alternative embodiment of the main body portion of the present invention, tissue-facing surfaces 30 are formed of polymeric fibers 54 which are woven into a gauze net fabric 53. A thin layer 50 of pure titanium coats each polymeric fiber 54 constituting the gauze net fabric.

Figure 11:
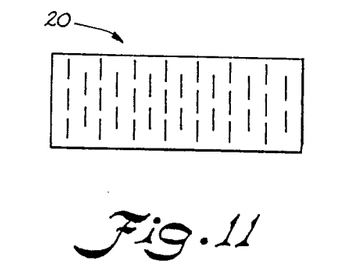
FIG. 11 is a top plan view of still another alternative embodiment of the apparatus of the present invention.
Figure 11A:
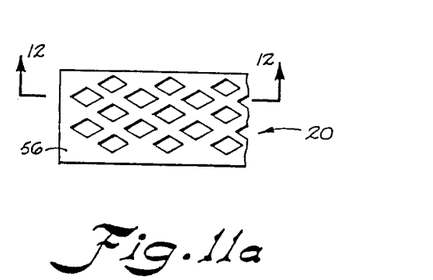
FIG. 11a is a partial top plan view of the apparatus of FIG. 11 in a stretched condition.
Figure 12:
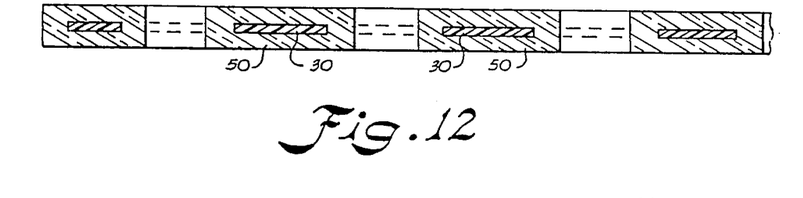

As shown in FIGS. 11, 11a, and 12, another alternative embodiment of the main body portion of the present invention includes tissue-facing surfaces 30 which are formed of an expanded polymeric film 56. A thin layer 50 of pure titanium coats the tissue-facing surfaces of the expanded polymeric film. One suitable polymeric material for the expanded film structure of FIGS. 11, 11a and 12 is poly-tetra-fluoro-ethylene.

Figure 13:
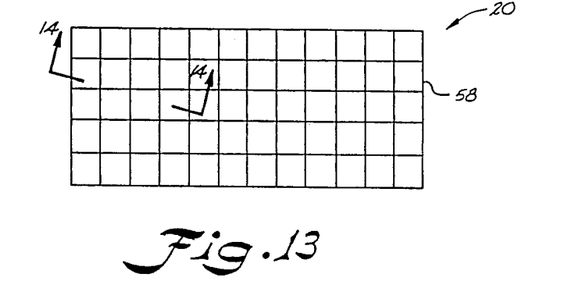
FIG. 13 is a top plan view of a further alternative embodiment of the apparatus of the present invention.
Figure 14:
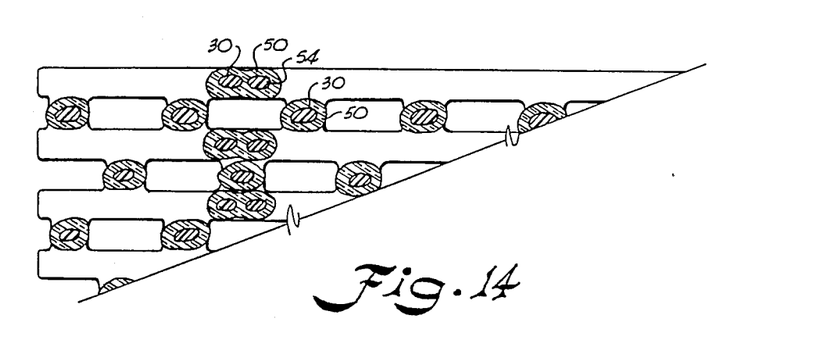
FIG. 14 is an expanded cross-sectional view taken along the lines 14—14 of FIG. 13.

As shown in FIGS. 13 and 14, another alternative embodiment of the main body portion of the present invention comprises a fabric 58 formed of spun-bonded or heat-bonded polymeric fibers 54 which comprise the tissue-facing surfaces of the main body portion of the present invention. As shown in FIG. 14, the spun-bonded or heat-bonded fabric includes polymeric fibers 54 having exterior surfaces comprising tissue-facing surfaces 30 which are coated by a thin layer 50 of pure titanium. As further illustrated in FIG. 14, the spun-bonded or heat-bonded fabric can comprise many different layers and many geometric arrangements between adjacent layers, as desired.

Figure 15:
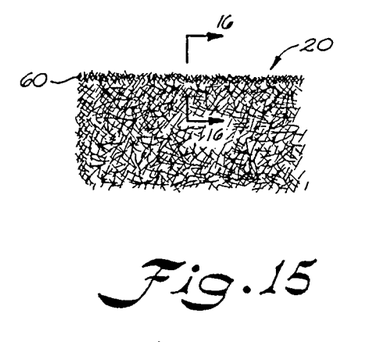
FIG. 15 is a top plan view of yet a further alternative embodiment of the apparatus of the present invention.
Figure 16:
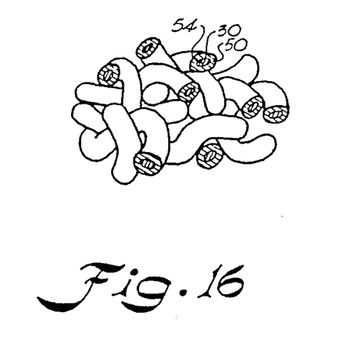
FIG. 16 is a detail perspective view taken along the lines 16—16 of FIG. 15.

In yet another alternative embodiment of the main body portion of the present invention shown in FIGS. 15 and 16, for example, a plurality of polymeric fibers are intertwined to form a felt fabric 60. Polymeric fibers 54 have tissue-facing surfaces 30 which are coated by a thin layer 50 of pure titanium.

Figure 4:
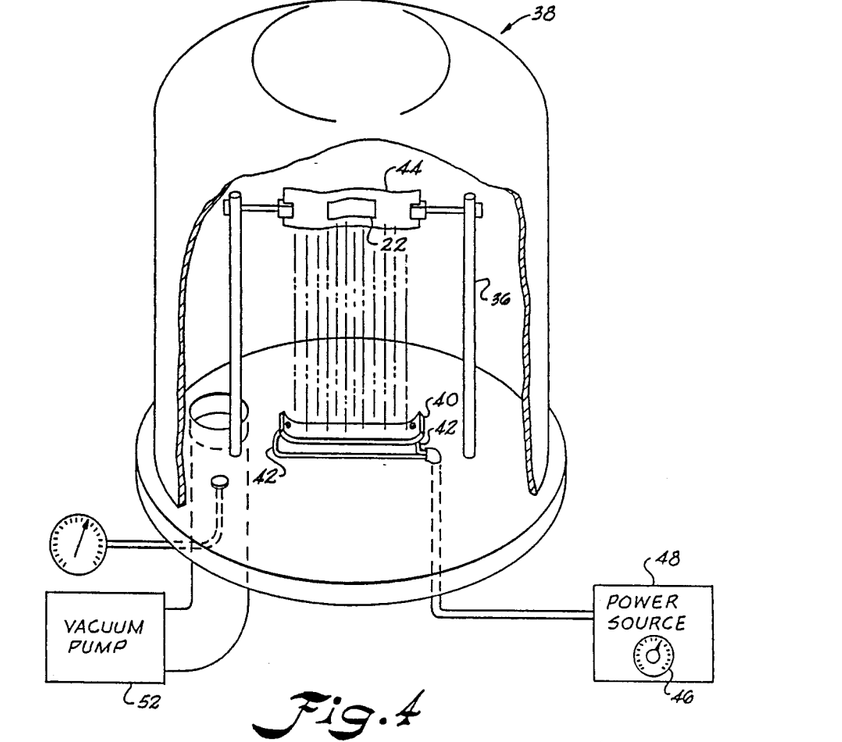
FIG. 4 illustrates an embodiment of apparatus for carrying out an embodiment of the method of the present invention.

In accordance with the method of promoting tissue adhesion of a host's soft tissue bed to a soft tissue implant having a main body portion with tissue-facing surfaces, there is provided the step of coating the tissue-facing surfaces of the main body portion with a layer of pure titanium. Preferably, the layer of pure titanium comprises a thin film 50 of about one micron of pure titanium which covers the tissue-facing surfaces of the main body portion. The titanium coating step preferably comprises vapor deposition of a thin film 50 of about 1 micron thickness of pure titanium on the tissue-facing surfaces of the main body portion. One embodiment of a vapor deposition process of applying a titanium coating is illustrated in FIG. 4 and described in greater detail in the EXAMPLE which follows.

The requisite titanium coating also can be applied to the tissue-facing surfaces of the main body portion by methods other than the vapor deposition method. For example, an intermediate coating of a coupling agent can be applied to the tissue-facing surfaces of the main body portion so that a titanium layer will more readily and more permanently adhere to the coating comprising the coupling agent. Two other alternative methods for applying the titanium coating to the tissue-facing surfaces are (1) cathodic sputtering and (2) decomposition deposition of titanium. In addition, while Applicants have not performed the titanium coating step using an electroplating method, Applicants believe that such a method may also yield a satisfactory result.

In further accordance with the method of the present invention, the implant is sterilized after having been coated with titanium. One embodiment of the sterilization step is explained in detail in the EXAMPLE.

In still further accordance with the method of the present invention, the implant is implanted into a host's soft tissue bed. The details of one embodiment of the implantation step are discussed below in connection with the EXAMPLE.

The following example is presented to illustrate the present invention, but the present invention is not limited to this example.

EXAMPLE

Substrate Preparation

PET velour fabric strips with dimensions of 1 cm by 7.5 cm by 1.0 mm, were placed in an ultrasonic cleaner containing a low residue detergent (Liquinox, Alconox, Inc., New York, N.Y.) in distilled water for 6 hours. This was followed by three successive rinses with fresh distilled water at 10 minute intervals each. The strips were placed in a Soxhlet extractor at a temperature less than 30° C. and refluxed with distilled water for 24 hours. They were then placed in a sterile Petri dish and allowed to dry in a room temperature desicator for several days followed by individual packaging and sterilizing with ethylene oxide. They were allowed to degas in vacuum for 48 hours and stored in a dust-free environment. The PET velour strips were handled with forceps at all times.

Vapor Deposition of Coating of Titanium Layer (FIG. 4)

Before sterilization, cleaned PET velour fabric strips 22 were selected for titanium coating by vacuum evaporation. Implant strips were removed from a double sterilization bag and pinned to an aluminum foil-covered styrofoam block 44. The back side of the implant strip was coated first. The block was positioned on top of a stand 36 such that the velour strip was directly facing the source in a vacuum evaporator 38. The approximate angle of incidence from the source to the plane of the strip was 90°. A strip 40 of pure titanium metal (cp. AMS 4902, Grade 1, 35A, TICO Titanium, Court Farmington, Mich.) with approximate dimensions of 1.3 cm by 1.3 cm by 0.038 cm was placed across a pair of electrodes 42 and served as the source of evaporant. This system was placed under a vacuum of about $2 \times 10^{-5}$ Torr during evaporation by a vacuum pump 52.

The titanium strip used as the source was evaporated by resistance heating. The evaporating temperature of titanium was reached when the strip was yellow hot. The current was adjusted by a control 46 of a power source 48 to control the rate of evaporation. Since it varied with the cross-sectional area of the titanium strip, a current of about 150 Amperes was applied. The current was held constant until the PET velour fabric strip was completely covered with titanium as indicated by a greyish color on the surface of the velour strip. This procedure usually took about 5 minutes. However, a break in the titanium strip occasionally occurred and such occurrence abruptly terminated the evaporation. By experience, these strips were discarded when there was an insufficient coating thickness (i.e., color intensity). Once coated, the system was allowed to cool for 1 minute and then returned to atmospheric pressure. A new titanium strip was used for each evaporation. The coated implant strip was carefully unpinned and turned over, making sure that only the ends of the strip were handled with forceps. The back of the implant strip was coated following the same procedure as described above. The titanium-coated strips were further cut into 1 cm by 2 cm rectangles. They were then cleaned by the same procedure as before, except that the ultrasonic cleaning was decreased to 30 minutes.

The evaporant can be placed in a high melting point source such as tungsten or tantalum baskets (or boats). This is then connected in place between electrodes and is subsequently heated when a current is applied. When enough heat is applied by the source, the evaporant changes from a solid state to a vapor state. This entire evaporation process must be performed inside an evacuated chamber held at a very low pressure of $10^{-5}$ Torr in order to reduce the probability of contamination. Contaminants such as hydrogen, nitrogen, oxygen, carbon dioxide and water vapors are known to affect the rate of evaporation of the film by interacting with the substrate and the evaporant. Furthermore, at low pressure or vacuum, the vapor atoms can leave the evaporant relatively unimpeded and travel to the substrate with a long mean free path.

Since the evaporation process is performed at low pressures, the evaporant usually vaporizes at temperatures well below its melting temperature. For instance, titanium melts at a temperature of 1727° C. However, it evaporates at significant rates at temperatures above 1546° C. In general, the rate of evaporation is directly dependent on the vapor pressure and mass of the evaporant. It should be noted that once the temperature provides the evaporant with enough energy, the atoms can leave the evaporant. The energy required to overcome the attractive force between atoms of the evaporant is called heat of vaporization. As a standard operating technique, the evaporant is heated until its vapor pressure is approximately $10^{-5}$ Torr. At this vapor pressure, the atoms can leave most evaporants at a reasonable rate.

Practical limits, however, are sometimes set by the source which holds the evaporant. The evaporating process requires that the source have a melting point significantly higher than the temperature at which the evaporant vaporizes and that no wetting between the source and evaporant occurs. Unfortunately, titanium wets tungsten, and this results in film deposits containing traces of tungsten. When tantalum was used as a source, the deposited titanium film was found to be pure. However, tantalum tends to burn out during the premelting of titanium before the temperature required for evaporation has been reached. In order to consistently evaporate a thin layer 50 of pure titanium onto the PET velour fabric, titanium must be evaporated directly without the use of a source. (FIG. 4).

The deposition process takes place immediately after vaporization of evaporant atoms. Initially, nuclei are formed at isolated areas on the surface of the substrate. Each nucleation site consists of small numbers of atoms. These nuclei grow three-dimensionally and form isolated grains or crystallites. The film that is deposited at this stage is often referred to as an island film. As deposition progresses, there is a continuous growth of existing nuclei and formation of new nuclei. Eventually, the nuclei join together and form a continuous film which is very porous in nature. These pores may be filled if the evaporant is further deposited onto the surface.

Nature of the Titanium Layer

The structure of the deposited titanium film resembles the structure of a solid which is formed using metallurgical techniques of solidification. When evaporation takes place at low pressure, the resulting titanium film has a hexagonal, close packed crystal structure similar to that of bulk titanium. Because titanium oxide has a very high heat of formation, an oxide film immediately forms on the surface of this film despite its thickness. It is believed that the oxide layer formed on a titanium film in the presence of air at 20° C. is about 2 nm thick after 20 hours of exposure and reaches a thickness of 3.5 nm after one month. Furthermore, the titanium film that develops is believed to have a random polycrystalline structure with variable grain sizes. These grains are so much smaller than normally seen with bulk metals, that they are almost indistinguishable from the amorphous state.

The crystallographic nature (amorphous, polycrystalline or single crystalline) of the underlying substrate is believed to have a direct influence on the orientation of thin film crystallites. For example, with some single crystal substrates, the growth and joining of the nuclei tend to form crystals with a single orientation, and this results in a film with no grain boundaries. Similarly, amorphous substrates tend to promote the formation of amorphous films or very fine grains. For polymer substrates such as PET velour fabric, the titanium film is believed to develop into a randomly oriented polycrystalline structure.

The binding forces between the substrate and the evaporant are known to increase with the number of initial nuclei and therefore affect the coalescence and the size of the crystallites or grains. Increasing the rate of evaporation seems to have the same effect on grain size. X-ray analysis of the vapor deposited titanium layer was found to be identical with that of pure hexagonal titanium ($a=2.95$ Angstroms and $c=4.67$ Angstroms). In its oxidized form, the titanium thin-film had a tetrogonal rutile modification of titanium dioxide ($a=4.58$ and $c=2.98$). A high rate of deposition is known to increase the number of atoms introduced to the surface per unit of time and thus increases the number of nuclei formed from which a fine grained deposit grows. With a very slow rate of evaporation in a poor vacuum, the evaporated film possessed a structure similar to a NaCl cubic crystal ($a=4.20$). Both oxygen and nitrogen atoms filled the interstitial spaces.

The surface topography of thin films is known to be affected by varying the rate of evaporation and the incident angle of the vapor stream. It has been shown that films of varying roughness can be produced by changing the rate of evaporation. A film that is deposited in 2 seconds tends to be less granular than a film of the same thickness deposited in 20 minutes. A high incidence angle of the evaporant atoms relative to the substrate also leads to a textured surface. When the evaporant is directly above the substrate (90° incidence), the vapor atoms tend to distribute themselves evenly on the surface. With a high degree of incidence (i.e., 10°), the vapor atoms are deposited unevenly, forming islands which lack symmetry.

After the deposition process, the performance of the substrate is strongly dependent on the adherence of the thin film to the substrate. According to ASTM standards (D 907-70), adhesion is "a state at which two surfaces are held together by interfacial forces." For metal-polymer systems, electrostatic bonding has been suggested to be the principal mechanism for adhesion.

The oxygen-active titanium thin-film has been known to be highly adherent to glass, ceramics and other oxygen bearing substrates. It has been reported that the surface chemical composition of PET velour fabric and Mylar are very similar. Both types of polyethylene terephthalate bore 30% oxygen.

Experimental Animals

Female New Zealand White rabbits obtained from the same local breeder were used for all implantations. They were given food and water ad libidum. From healthy animals, twelve were chosen for experimental surgery and designated for two explantation periods. Six rabbits (JD, JE, JJ, JK, JL and JM) were randomly picked for ten day studies, and six (JB, JC, JF, JG, JH and JI) were picked for twenty-eight day studies.

Implantation Sites

After the implants were coated with titanium, they were recleaned and sterilized before implantation. A total of three titanium-coated (test) specimens and one non-coated (control) specimen were randomly implanted at multiple sites in the subcutaneous tissue at the dorsum of each experimental animal. There were a total of eight sites, each covering an approximate area of 16 $cm^2$. These sites were arranged in two rows of four, left and right of the spine. Sites 1 and 5, for example, were located just below the scapula while sites 4 and 8 were located just above the hips of the animal.

Animal Anesthetizing

Before surgery, each animal was taken off food while still allowing water. The animals were tranquilized with 2 mg/kg by weight of acetylpromazine maleate (Aveco Co., Inc., Fort Dodge, Iowa). The hair on the back and flanks of the animals was shaved from the scapula to the hip. Loose hair was removed by vacuum. The animals were then further tranqulized to a point of surgical analgesia and relaxation with an intramuscular injection of 55 mg/kg by weight of ketamine Hydrochloric acid (Ketaset, Bristol Laboratory, Syracuse, N.Y.). An antibacterial ointment (Bacitracin-Neomycin-Polymyxin, Neobacimyx, Burns-Biotec Laboratories, Inc., Omaha, Nebr.) was applied to each animal's eyes to prevent eye dehydration and infection. The animals were then tatooed for identification purposes and transported from the preparation room to the operating room.

Animal Surgery

The animals were placed in ventral recumbancy and prepared for sterile surgery. The shaved area was circumferentially scrubbed with three alternating tamed iodine solution (Betadine Surgical Scrub, Purdue Frederick Co., Norwalk, Conn.) and 70% ethanol soaked gauze sponges. At the end of this procedure, the entire area was sprayed with a more concentrated Betadine solution and draped with sterile towels.

A 5 cm incision was made along the dorsal midline of the animal approximately midway between its scapula and hip with a #10 scapel blade. The incision extended down to the superficial fascia. Bleeders were controlled by meticulous hemostasis. Four subcutaneous pockets were then created by blunt dissection with Metzenbau scissors.

Implantation

Each of the four standard sterilized implants previously soaked in saline was secured by Aliss clamps. These implants were positioned in their pre-selected pockets with the utmost care to avoid contact with the skin or folding of the rectangular implants. The midline incision was then closed. A polyethylene terephthalate green braided cardiovascular suture (Ethiflex, Ethicon Inc., Somerville, N.J.) was used for subcutaneous closure. The skin was closed with stainless steel staples.

Post Operative Care

Upon completion of the surgical procedure, the animals were placed in an incubator which was maintained at a constant temperature of 26° C. When the animals fully recovered from the anesthesia and appeared to be in stable condition, they were returned to their respective cages. Food and water were provided ad libidum. The animals were examined daily for any signs of inflammation.

Animal Sacrifice

The animals were electively sacrificed at 10 and 28 days with a lethal dosage (5 cc) of sodium pentobarbital (Socumb-6 GR, Butler Co., Columbus, Ohio). This drug was injected intracardically. The animal was then weighed and the new growth of hair on the area surrounding the surgical sites was shaved. The skin of the back was excised. The implantation sites were grossly examined for pathological changes. The four implants with surrounding tissue were then retrieved for microscopic examination.

Implant/Tissue Examination Procedure

The retrieved titanium coated (test) samples were prepared for three histological techniques: (1) standard light microscopy, (2) enzyme histochemistry and (3) transmission electron microscopy. The non-coated (control) specimens, however, were only prepared for standard light microscopy.

In each hematoxylin and eosin-stained slide, the presence or the absence of blood vessels and various cell types, namely mononuclear cells (i.e., fibroblasts, monocytes and macrophages) and foreign body giant cells and their corresponding location within the velour were first recorded. Parameters were then set up to account for cellularity. These parameters described the number of cells and the uniformity of distribution of these cells in the interstices of the velour. Four parameters were selected to describe the cellularity or the cellular distribution within the interstices and are as follows: (1) No cells within the confines of the velour interstices; (2) Low number of cells non-uniformly distributed within the interstices (less than 7 cells); (3) High number of cells non-uniformly distributed within the interstices (more than 6 cells); and (4) High number of cells uniformly distributed within the interstices (more than 6 cells).

It should be noted that the number of cells within the latter three parameters was not selected arbitrarily, but represents the cellularity of the granulation tissue which was observed to surround 10 day control and test implants. Parameter 3 appeared to describe these granulation tissues well. The number of mononuclear cells within the confines of the designated field (0.01 mm$^2$) was also recorded for this particular staining technique.

The number of foreign body giant cells was counted in five different fields along the length of the velour. Another predetermined field was selected for these cell types, and this field covered a larger area (0.025 mm$^2$) on the outermost aspects of the velour.

The arrangement of collagen-positive stained materials within the interstices was first examined qualitatively. A total of five different parameters were selected to semi-quantitatively describe these arrangements and are as follows: (1) Amorphous-like substances (either mucus or serum); (2) Array of short collagen fibers arranged in a disorderly fashion; (3) Low density collagen strands dispersed in a matrix-like configuration; (4) High density of collagen strands inter-connected with one another; and (5) Compact formation of thick collagen strands.

The arrangement of reticular fibers impregnated with silver from Gomori's silver stain were first examined and semi-quantitative parameters were assigned as follows: (1) Fine black fibers which appeared as multifilaments but lacked any organization; (2) Fine black fibers which appeared as multifilaments arranged in an organized network. Granules were observed at regular intervals along these fibers; (3) Semi-thick black stained fibers where multifilaments were loosely embedded in fine black fibers; and (4) Clusters of semi-thick black fibers.

Transmission electron micrographs at various magnifications were examined. The ultrastructure of tissue components within the limited field of study was first evaluated qualitatively. The mean diameters of collagen microfibrils and the interfibrillar spacing of normal subcutaneous tissue, scar, capsule and tissue ingrowth in the interstices of the non-coated and the titanium coated implants were then manually measured on the photomicrographs with a micrometer. The mean diameter of reticular fibers was also determined.

Evaluation of Implantation Sites

Macroscopic evaluation of the implantation sites at necropsy revealed very mild signs of local inflammation. Inflammation appeared to be somewhat more pronounced around the titanium-coated PET velour fabric implants (sometimes referred to a test samples) than around the non-coated PET velour fabric implants (sometimes referred to as control samples). This was judged on the basis of the milky colored tissue capsule and the degree of vascularization around the implants.

Cell Densities

In the interstices of the 10-day control samples (no titanium coating), each of the majority of the foreign body giant cells (FBGC) exhibited 5 or less nuclei and was located in one of the outermost pores of the implant directly apposing the fibrous capsule which surrounded each implant. On occasions, multinucleated cells were found at areas with a high density of PET fibers. FBGC were similarly distributed within the interstices of the test samples (with titanium coating) at 10 days. However, cell densities in the interstices of the 10 day coated and non-coated samples were significantly different. The 10-day titanium coated implants had much higher cell density within the outermost pores than the 10-day non-coated implants. At 28 days there was a striking difference in the apparent size of these cells within the interstices of the coated samples. Some of these cells exhibited 20 or more nuclei and were found attached to more than one titanium coated PET fiber.

When cell densities were compared there was no difference found between 10 and 28 days implantation in the control or test implants. However, between 10 and 28 days, there was a shift of cell distribution from the implant periphery to the center of the titanium coated implants. This might be an indication that cells are still migrating from the periphery into the interstices between 10 and 28 days in the coated implants, but not in non-coated implants.

There were basically two populations of mononuclear cells in the interstices of the test and control samples. These cells consisted of mononuclear phagocytes and fibroblasts. A few polymorphonucleated leucocytes were also observed. In the 10 day and 28 day noncoated samples and the 10 day coated samples, mononuclear cells were predominantly found near the surface of the velour. A low cell density was observed deep in the interstices. At 28 days, the coated samples contained a relatively high cell density in the deeper velour areas. In one case, fat cells were seen at this location. A high number of mononuclear cells was also found near the surfaces of the 28 day non-coated samples and in the 10 and 28 day titanium coated samples. Mononuclear cell densities at the surface of all 4 tissue samples were found to be significantly different from each other. However, when comparing the cellularity ratings at the surface of these velour samples using the hematoxylin and eosin staining technique, only the mean ratings of cellularity in the 10 and 28 day titanium coated samples were not significantly different.

Collagen Organization

After implantation of the test (titanium coated) and control (noncoated) samples for 10 days, the interstices were found to be filled with a fine network of collagen fibers. This network was not yet organized into bundles and resembled a flimsy fish-net. The extracellular matrix in the interstices of the 28 day non-coated samples was almost indistinguishable from the 10 day samples, with no apparent progress in collagen organization (maturation). There was no significant difference between the mean ratings of collagen for the non-coated implant samples. By 28 days, the titanium coated samples contained more and better organized collagen bundles. The differences in the mean rating of collagen in the 28 day titanium coated samples and the mean ratings of collagen in the three non-coated tissue samples were highly significant ($p < 0.05$).

A range of collagen organization was observed in the interstices of the 28 day titanium coated samples from animal to animal and site to site. There were two cases out of the six coated tissue samples which exhibited poor collagen organization and growth, resembling that found in the 28 day non-coated control samples. These six coated samples also exhibited low densities of mononuclear cells. Thick collagen strands and a high infiltration of cells were, however, observed in the interstices of the other titanium coated 28 day samples. Both collagen bundles and elongated cells were observed to be randomly oriented in the interstices of the titanium coated samples. Thick collagen strands were also seen encapsulating individual titanium-coated fibers. The proliferation of collagen appears to occur in conjunction with the influx of mononuclear cells and with the formation of foreign body giant cells.

Reticulin Formation

In the 10 day non-coated samples, reticular fiber formation in the interstices of the velour was in general uniform. In most areas, there was a sparse network of reticular fibers which were silver stained impregnated minute filaments.

When the non-coated samples were implanted for 28 days, reticulin formation was non-uniform. A two-fold increase in the amount of dispersion of the ratings was observed from 10 to 28 day coated and non-coated samples. It was determined that the mean rating of reticulin in the 10 day non-coated samples was significantly different from the mean ratings of reticulin in the three coated implant types. However, the 10 and 28 day titanium coated samples were not significantly different from one another. Capillaries In the interstices of the non-coated samples at 10 and 28 days, there were few capillaries. On the other hand, the 10 day coated samples showed an abundance of capillaries throughout their interstices. Not only was there an increased number of capillaries, the diameter of these blood vessels also increased, varying from 10 to 40 microns.

Results of Transmission Electron Microscope Examination

Transmission electron microscopy confirmed the light microscopic findings and provided some ultrastructural details on the organization of the extracellular tissue components in the velour interstices. The tissue in the 10 and 28 day non-coated implants displayed few cells, and these cells were predominantly macrophages. The majority of these macrophages were in the process of fusion with one another to form foreign body giant cells. They appeared to be active in phagocytosis, possessing numerous vacuoles, lysosomes and multiple filopodia. Fibroblasts could not be identified in the interstices. However, an abundance of elastic fibers and short collagen microfibrils distributed in a highly disordered fashion, were observed.

At 10 days, the tissue in the coated samples somewhat resembled that found in the 10 day non-coated implants. A disorderly array of collagen microfibrils filled the interstices. Capillaries were found directly adjacent to titanium-coated PET fibers. During the next eighteen days, the space between the titanium-coated fibers was filled with a mixture of active macrophages and fibroblasts. The macrophages showed similar characteristics as those found in the interstices of the non-coated implants. They possessed numerous vacuoles and cytoplasmic processes (filopodia). Fibroblasts, virtually absent in the non-coated samples, were present and shared the space with macrophages. In addition to having a large number of rough endoplasmic reticula within their elongated cytoplasm, these cells were found adhered to and spread over the surface of titanium-coated PET velour fabric fibers. In the non-coated PET velour fabric specimens, no macrophages or fibroblasts were spread over the surface of the PET velour. In general, an increase in cell density corresponded with an increase in organization of collagen molecules.

In the 28 day titanium coated implants, collagen microfibrils were found loosely arranged in aggregates or packed in dense fibrils or encapsulating the titanium-coated PET fibers. An amorphous film, ranging from 33 nm to 130 nm thick, was found at the interface between the collagen fibrils and the titanium-coated fibers. On a few occasions, small aggregations of collagen microfibrils were observed to be in the process of being phagocytised by macrophages. These cells were also found in the lumen of capillaries. Reticular fibers were observed as a loose delicate network (reticulum) and found circumferentially around the PET fibers. The reticular fibers were also separated from the titanium coating by an amorphous film ranging from 55 to 222 nm thick. Large capillaries were also observed in the interstices of the titanium-coated PET velour fabric implants.

Scanning electro micrographs revealed the presence of holes and cracks along the contour of the titanium-coated PET velour fabric fibers, possibly a result of the coating process and preparation of coated samples for SEM. Excessive charging of the surface occurred when the titanium-coated samples were exposed to the electron beam. This might be indicative of a failure to coat all the fibers on the surface and deep in the interstices of the velour with titanium. The exact topography of a PET velour fabric fiber has not yet been determined. From transmission electron micrographs, the titanium coating appeared slightly rougher in some areas than others at the micron level of resolution. The titanium coating was determined to have a thickness of approximately 60 nm. The mean diameter of titanium-coated PET velour fabric fibers was measured to be $17\pm2$ microns (n=40) using two scanning electron micrographs, each with a calibrated microsphere.

Electron micrographs were also used to compare the diameter of collagen microfibrils and reticular fibers from various tissue samples with those found in the interstices of the titanium coated and the non-coated implants. The mean diameter of collagen microfibrils and their corresponding interfibrillar spacing was determined. In addition, the mean diameter of reticular fibers around the titanium-coated PET fibers was also determined. Collagen microfbrils from granular tissue in the implant surrounding capsule were observed to increase in diameter from day 10 to day 28. In comparison to normal subcutaneous tissue ($71\pm9$ nm), the mean diameter of these microfibrils was comparable ($78\pm19$ nm). Collagen microfibrils in the interstices of the titanium coated samples increased up to threefold in mean diameter thickness from 10 to 28 days.

Initially, the organization of collagen in the interstices of the 10 day titanium-coated PET velour fabric was similar in appearance when compared to that found in 10 and 28 day non-coated fabric. However, as the granulation tissue developed, a higher content of PAS-positive stained tissue components as compared to acidic glycosaminoglycans was observed. A higher infiltration of mononuclear cells and more rapid formation of foreign body giant cells were also observed near the surface of the titanium-coated velour. In addition, more capillaries were located in the interstices and may have aided in the removal of the initial fibrin meshwork, thus improving conditions for the growth of more mature fibroblasts. These vessels may also have provided for better metabolic and nutritional conditions for fibroblastic activity in the implant pores soon after the disappearance of the immature cells. The described tissue in the titanium-coated samples generally appeared to develop into a mature granulation tissue.

Although the final stages of foreign body wound healing had not been fully achieved in 28 days, the tissue in the interstices of the titanium coated fabric was significantly different from the non-coated specimens. As observed during the maturation of granulation tissue, collagen appeared to be rapidly secreted by highly proliferative fibroblasts now present in these wounds. The diameter of the largest collagen microfibrils found around the titanium coating was comparable in thickness with the microfibril diameters of the fibrous capsule representing the more mature scar tissue. At other areas in the interstices of the titanium coated fabric, small aggregations of microfibrils were similar in thickness to those found in immature scar tissue.

Adhesion of Host Tissue to Titanium Layer

Of greater significance was the observation that collagen fibrils were seen in close proximity to and surrounding the titanium-coated PET velour fabric fibers. Not only did these fibrils encapsulate the PET fibers, there also existed an amorphous film which appeared to bond the titanium coating with fibrous collagen and reticulin. Electron microscopic analysis indicated the presence of sulfated glycosaminoglycans as an amorphous mass and its involvement in the attachment of both collagen and reticulin to the titanium coating. The attachment of these tissues should facilitate anchoring the titanium coated implant to the tissue bed of the host.

Fibroblasts found in granulation tissue have been reported to exhibit a distinct polarity. They have been suggested to migrate in the same general direction as their long axis, usually towards the unhealed wound. A similar unidirectional cellular polarity was observed in the interstices of the 28 day titanium-coated implants. This further suggested that the tissue in the interstices resembled that of granulation tissue and that fibroblasts were in the continued process of migrating toward less developed areas in the velour.

Macrophages in the interstices of the titanium-coated PET velour fabric may have been more activated by the titanium coating than by the untreated polyethylene terephthalate. The modified surface of PET velour fabric created by coating individual PET velour fabric fibers with titanium apparently provoked a local increase in the number of macrophages and activated these cells to stimulate fibroblast proliferation, collagen synthesis, and neovascularization.

A local increase in macrophage numbers in the interstices of the titanium-coated PET velour fabric was associated with an increase of fibroblasts and fibroblastic activity. The fibroblasts shared the spaces existing between the titanium-coated PET fibers with macrophages, giant cells and capillaries.

After coating the PET velour fabric fibers with pure titanium, the resulting in growth of tissue was histologically different from that found in non-coated PET velour implants. The titanium coating provoked an increased number of interfacial cells consisting of an almost equal distribution of macrophages and fibroblasts. In addition, foreign body giant cells were also noticeably present.

The tissue in the titanium-coated PET velour fabric implants matured progressively. Initially (at 10 days) the tissue in growth somewhat resembled those found in non-coated PET velour fabric implants. At 28 days, the tissue in growth was observed to possess ultrastructural characteristics similar to more mature granulation tissue, although the end stage of development of scar tissue had not been reached. The formation of collagen fibrils and the presence of numerous blood vessels in the interstices of the titanium-coated PET velour fabric implants indicated healing was in progress and that mature granulation tissue was developing.

Adhesion Testing of Titanium Layer to PET Substrate

To test the adhesion of the titanium thin-film to a PET velour fabric fiber, a simplified model was developed. Mylar (E.I. Dupont de Nemours Co., Inc.) was used in place of PET velour fabric to take advantage of Mylar's flat surface and its identical chemical composition. A sheet of Mylar, approximately 50 microns in thickness, was cut into 5 cm by 7 cm strips and prepared by the same procedure as the PET velour fabric implants including cleaning and coating procedures, but excluding sterilization. The sheets were coated on both sides with titanium. The coated strips of Mylar were then cleaned using the same procedure as the titanium-coated PET velour fabric strips after evaporation, except that they were cleaned in the Soxhlet extractor for 48 hours. After the strips were thoroughly dried, they were cut into approximately 2 cm by 2 cm square strips. They were placed between the ends of two cold rolled steel rods and glued in place with epoxy cement.

During tensile testing, a jig was used to align the applied force with the axes of the rods. The applied force was thus perpendicular to the titanium thin-film. To avoid inadvertent shear stresses which would immediately disrupt the titanium-Mylar interface, the two rods remained in this fixture until they were tested. A constant compressive load was applied to the rods during curing so that a consistent epoxy thickness was obtained for all samples. The samples were allowed to cure for 24 hours. Film areas not in direct apposition with the surface of the rods were trimmed away. A universal joint was used to allow proper alignment of the tensile force during testing. The tensile tests were performed in air at room temperature using a testing machine (Instron, Canton, Mass.) with a deflection rate of $8.25 \times 10^{-4}$ cm/s.

The adhesion of the titanium thin-film on Mylar appeared to be satisfactory. Despite 24 hours of exposure in an ultrasonic cleaner, the greyish color of the titanium coating did not fade. However, when the implants were not handled with forceps during the manufacturing process, the coating disintegrated. It was therefore considered important to clean the velour thoroughly from contaminants and avoid contact of oily substances with the PET or Mylar strips before the evaporation procedure.

After refluxing the titanium-coated specimens for a total of 48 hours in distilled water at 30° C., the titanium coating still adhered well to the Mylar, as confirmed by a mean pull strength of $2.83 \times 10^6$ Pa. A large standard deviation of $1.31 \times 10^6$ Pa (n=5) was observed. Under an optical microscope, the detachment of the rods was observed to be due to a combination of adhesive failures. At some areas of the loaded surface, the titanium coating pulled away from the Mylar. In other areas, failure occurred at the interface between the epoxy and the surface of the steel rod. In most cases the failure occurred partially at the titanium/Mylar interface and partially at the steel/epoxy interface. In no case did failure occur at the titanium/epoxy interface. In these tests, the maximum failure stress never exceeded $4.59 \times 10^6$ Pa. For the sake of comparison, the two rods were joined with the same epoxy and loaded with the same deflection rate of $8.25 \times 10^{-4}$ cm/s. A tensile stress of $4.53 \times 10^6$ Pa was required to pull the two rods apart. This suggests that the method may have given a false indication of the bond strength whenever the stress exceeded about $4.5 \times 10^6$ Pa.

Due to chemical bonding and mechanical interlocking, the thin-film adhered to the Mylar with a substantial force. When the titanium coating extended all around the PET fiber, the interatomic forces between the titanium atoms may also contribute to the stability of the coating. In addition, the observed large standard deviation in force measurements has been suggested to be influenced by the cement thickness at the joint, the curing cycle, and the amount of catalyst used in the cement.

The histological preparation methods for light microscopy appeared to chip the titanium coating off the PET velour fabric fibers. Titanium chips were observed in the staining solution and smeared over the tissue sections. The tight adherence of the coating to the PET velour fabric fibers was confirmed by transmission electron microscopy. To determine the step at which the failure of the coating occurred during light microscopic processing, a non-implanted test sample was cleaned and processed following the same histological procedure as an implanted test sample. The coating-substrate interface was found to fail during or following thin sectioning of the paraffin-embeded test samples. Apparently, the knife applied a shear force which either took off the coating or loosened it.

If the surface of the velour fibers is adequately cleaned, it appears that the titanium-coating will retain its integrity when placed in a physiological environment.

It will be apparent to those skilled in the art that various modifications and variations can be made in the embodiments of the method and apparatus of the present invention without departing from the scope or spirit of the invention. Thus, it is intended that the present invention cover the modifications and variations of this invention coming within the scope of the appended claims and their equivalents.

What is claimed is:

1. A method of promoting tissue adhesion of a host's soft tissue bed to a soft tissue implant having a main body portion with tissue-facing surfaces, the method comprising the steps of:
   coating the tissue-facing surfaces of the main body portion with a layer of pure titanium;
   sterilizing the titanium coated implant;
   forming a thin layer of titanium oxide over the pure titanium layer as the free surface of the implant; and
   implanting the titanium coated implant into the host's soft tissue bed.

2. A method as in claim 1, wherein:
   said coating step comprises vapor deposition of pure titanium on the tissue-facing surfaces of the main body portion.

3. A method as in claim 2, wherein:
   said vapor deposition includes direct resistance heating of a pure titanium structure.

4. A method of promoting tissue adhesion of a soft tissue bed to the tissue-facing surfaces of a soft tissue implant wherein the tissue-facing surfaces are formed of a flexible polymeric material, the method comprising the steps of:
   coating the tissue-facing surfaces with a layer of pure titanium;
   sterilizing the titanium coated implant;
   forming a thin layer of titanium oxide over the pure titanium layer as the free surface of the implant; and
   implanting the titanium coated implant into the host's soft tissue bed.

5. A method as in claim 4, wherein:
   said coating step comprises vapor deposition of pure titanium on the tissue-facing surfaces.

6. A method of promoting tissue adhesion of a host's soft tissue bed to the tissue-facing surfaces of a soft tissue implant, wherein the tissue-facing surfaces are formed of a porous polymeric material, the method comprising the steps of:

coating the tissue-facing surfaces with a layer of pure titanium;

sterilizing the titanium coated implant;

forming a thin layer of titanium oxide over the pure titanium layer as the free surface of the implant; and implanting the titanium coated implant into the host's soft tissue bed.

7. A method as in claim 6, wherein:

said coating step comprises vapor deposition of pure titanium on the porous polymeric tissue-facing surfaces of the soft tissue implant.

8. A method of promoting tissue adhesion of a host's soft tissue bed to the tissue-facing surfaces of a soft tissue implant wherein the tissue-facing surfaces are formed of a polymeric material having a roughened surface texture, the roughness being hills and valleys in a range of 1 to 100 micron depths and widths, the method comprising the steps of:

coating the tissue-facing surfaces with a layer of pure titanium;

sterilizing the titanium coated implant;

forming a thin layer of titanium oxide over the pure titanium layer as the free surface of the implant; and implanting the titanium coated implant into the host's soft tissue bed.

9. A method as in claim 8, wherein: said coating step comprises vapor deposition of pure titanium on the roughened tissue-facing surfaces of the soft tissue implant.

10. A method of promoting tissue adhesion of a host's soft tissue bed to a soft tissue implant having tissue-facing surfaces formed of a polymeric fabric, the method comprising the steps of:

coating the tissue-facing surfaces of the polymeric fabric with a layer of pure titanium;

sterilizing the titanium coated implant;

forming a thin layer of titanium oxide over the pure titanium layer as the free surface of the implant; and implanting the titanium coated implant into the host's soft tissue bed.

11. A method as in claim 10, wherein:

said coating step comprises vapor deposition of pure titanium on the polymeric fabric.

12. A method of promoting tissue adhesion of a host's soft tissue bed to the tissue-facing surfaces of a strip of polyethylene terephthalate velour, the method comprising the steps of:

cleaning the strip with a low-residue detergent and rinsing same with fresh distilled water;

refluxing the strip in distilled water at a temperature of less than 30° C. for more than one hour;

drying the strip in a room-temperature desiccator for more than one day;

degassing, sterilizing, packaging and storing the strip in a dust-free environment;

removing the strip from the packaging and mounting the strip in a vacuum evaporator at an approximate angle of incidence of 90° from the source of the vacuum evaporator, said source comprising a pure titanium metal evaporant;

evacuating the vacuum evaporator to a vacuum of about $2 \times 10^{-5}$ Torr;

resistance heating the titanium evaporant until the strip is coated with a layer of pure titanium on the order of 1 micron thick;

resterilizing the titanium coated strip;

forming a thin layer of titanium oxide over the pure titanium layer as the free surface of the implant; and implanting the titanium coated strip into the host's soft tissue bed.

* * * * *